United States Patent [19]

Gancy

[11] 4,389,323

[45] Jun. 21, 1983

[54] PROCESS OF MAKING TWO UNIFORM GRADES OF CALCIUM MAGNESIUM ACETATE

[76] Inventor: Alan B. Gancy, 265 Robineau Rd., Syracuse, N.Y. 13207

[21] Appl. No.: 316,816

[22] Filed: Nov. 2, 1981

[51] Int. Cl.$^3$ .......................... C09K 3/18; C01F 5/00; C01F 11/00

[52] U.S. Cl. ..................................... 252/70; 423/158; 423/173; 423/175; 423/430; 423/593; 423/635; 106/13; 562/607; 562/608

[58] Field of Search .................. 252/70; 423/158, 173, 423/175, 430, 593, 635; 106/13; 562/607, 608

[56] References Cited

U.S. PATENT DOCUMENTS 4,239,736  12/1980  Fenske ............................... 423/173

Primary Examiner—John E. Kittle
Assistant Examiner—Robert A. Wax

Attorney, Agent, or Firm—Austin R. Miller

[57] ABSTRACT

A process of making different grades of calcium magnesium acetate deicing agents, having substantially uniform but different calcium-to-magnesium mole ratios, from limestone having varying proportions of calcium carbonate and magnesium carbonate, is provided wherein limestone containing calcium and magnesium carbonates is finely divided, mixed with water to form an aqueous suspension of limestone, vigorously agitated and reacted with excess acetic acid. The reaction is completed by adding to the reaction batch about 30% of the molar equivalent of calcined finely divided limestone base to produce a calcium magnesium acetate salt solution having a calcium-to-magnesium mole ratio much greater than one. The insolubles from this first reaction are removed, calcined and reacted with acetic acid in a second reaction to produce a calcium magnesium acetate salt solution having a calcium-to-magnesium mole ratio substantially equal to one.

6 Claims, 1 Drawing Figure

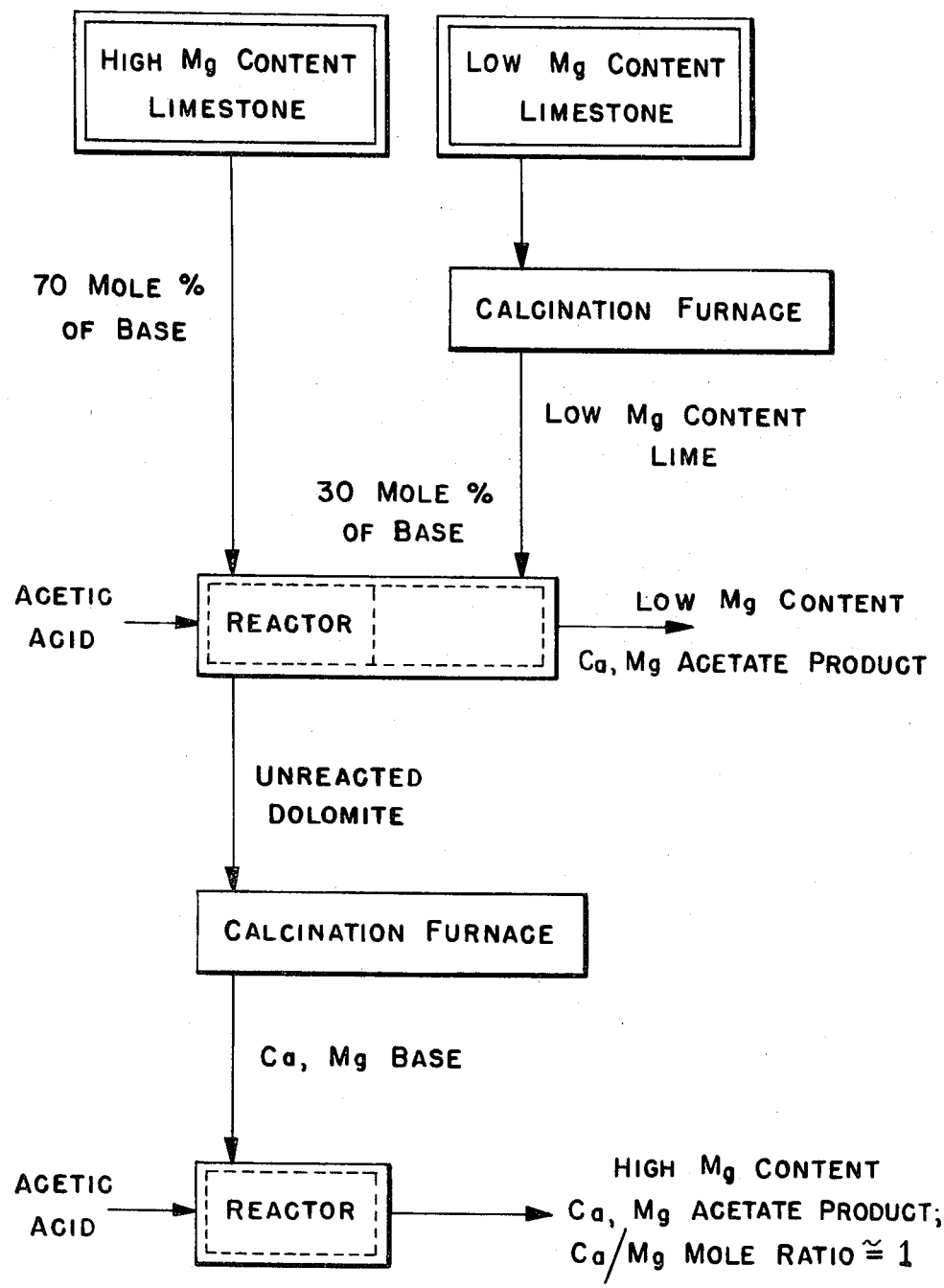

PROCESS OF MAKING TWO UNIFORM GRADES OF CALCIUM MAGNESIUM ACETATE

The subject matter of the present invention is related to the subject matter of my two copending applications, Ser. Nos. 319,473 and 333,037.

BACKGROUND OF THE INVENTION

1. Field of the Invention

This invention relates to a method of producing a calcium magnesium acetate (CMA) deicing agent, and further relates to such a method of making two uniform grades of CMA, one having a calcium-to-magnesium mole ratio substantially equal to one and the other having a calcium-to-magnesium mole ratio much greater than one.

2. Description of the Prior Art

U.S. Pat. Nos. 3,624,243 and 3,630,913, granted to Scott, Jr. et al both relate to chemical deicers containing magnesium and aluminum corrosion inhibitors making them especially suited for use on airport runways. Scott teaches the use of solutions containing urea, ethylene glycol, ammonium nitrate and water soluble chromate salts.

U.S. Pat. No. 4,163,079, granted to Beafore, teaches the spraying of belt transportation surfaces with a composition consisting of a water soluble polyhydroxide compound or a monoalkyl ether, and a water soluble organic compound having at least one hydrophilic group.

U.S. Pat. No. 4,245,166, granted to Glanville et al, discloses a composition for reducing the strength of ice consisting of from 5–90 wt.% of a water soluble organic compound selected from the group consisting of alkynols, diols, polyols, ketones, ethers, carboxylic acids and mixtures thereof; and from 1–20 wt.% of a substance containing ammonium ions selected from the group consisting of ammonium acetate, ammonium nitrate, ammonium sulphate, ammonium sulfamate, ammonium formate, ammonium cyanate, ammonium thiocyanate, ammonium carbonate, ammonium pentaborate, and mixtures thereof.

U.S. Pat. No. to Budenholzer et al, No. 2,918,052, teaches the use of metallic sodium and the caustic (NaOH) formed in the reaction of sodium and water, as a deicing agent. The exothermic nature of the sodium and water reaction, together with the freezing point depressant effect exerted by the caustic, results in a dual action deicing agent.

U.S. Pat. No. 4,081,256, granted to Donnelly, discloses a particulate composition which undergoes an endothermic reaction when mixed with water. This composition consists of urea, hydrated sodium acetate, potassium chloride or potassium nitrate, ammonium chloride and quar gum. Donnelly teaches the use of hydrated sodium acetate in applications requiring a reduction in temperature.

A major anticipated field of use for uniform grades of CMA is in the road deicing field. To date, road deicers have mainly consisted of sodium chloride. Although sodium chloride is quite effective as a deicing agent, it presents numerous difficulties and hazards.

Specifically, sodium chloride promotes corrosion of metallic parts and surfaces such as are found on automobiles and other machinery utilizing roads and highways. Furthermore, with the many millions of pounds of sodium chloride which are used on U.S. highways every winter, serious environmental and health questions are raised concerning plant and animal exposure to such large amounts of sodium and chlorine. This is especially relevant when large amounts of the sodium and chloride ions find their way into water ways and ultimately into human drinking water supplies.

Thus, there has been a need in the art for a road deicing agent substitute for sodium chloride which does not present these serious health and environmental questions.

It is anticipated that the major source of calcium carbonate to be used as a raw material in the manufacture of calcium acetates and calcium magnesium acetates is limestone. However, limestone in the United States generally contains small amounts (up to 20 wt.%) of dolomite (CaMg (CO$_3$)$_2$). Thus, any process which converts raw material limestone to calcium acetate must necessarily, without a prior costly separation step, produce an amount of magnesium acetate.

It has been found however that magnesium acetate also operates as an extremely effective road deicing agent. In fact, magnesium acetate is a more effective deicing agent than calcium acetate. Hence, it is extremely desirable to have a uniform calcium-to-magnesium mole ratio in the final deicing product in order to facilitate its use by the consumer. Unfortunately, because limestone will most likely be used as the commercial source of calcium and magnesium carbonate and because the proportion of dolomite in the limestone varies with the source of the limestone, the magnesium content of any deicer manufactured from limestone will necessarily vary with the source of the limestone used. In general, the magnesium content will always be lower than the calcium content, and in almost no case will the mole ratio of magnesium-to-calcium exceed unity. Because the product compositions will vary, the deicing characteristics will also vary.

Thus, there has been a need in the art for a process of making calcium magnesium acetate deicing agents, from limestone sources having varying amounts of calcium and magnesium carbonates, having uniform calcium-to-magnesium mole ratios.

OBJECTS OF THE INVENTION

Thus, it is an important object of the present invention to provide a safe, non-polluting, deicing agent and method of making same.

It is a further important object of the present invention to provide a method of making calcium magnesium acetate deicing agents, from limestone sources having varying amounts of calcium and magnesium carbonate, having relatively uniform calcium-to-magnesium mole ratios.

It is a further important object of the present invention to provide such uniform grade calcium magnesium acetate deicing agents having uniform deicing properties for easy and effective use by consumers.

SUMMARY OF THE INVENTION

A process of making different grades of calcium magnesium acetate deicing agents, having substantially uniform but different calcium-to-magnesium mole ratios from limestone having varying proportions of calcium carbonate and magnesium carbonate, comprises finely dividing limestone containing both free calcium carbonate and CaCO$_3$.MgCO$_3$, calcining some finely divided limestone, mixing said finely divided limestone with water to form an aqueous suspension of limestone, vigorously agitating said aqueous limestone suspension, reacting said aqueous limestone suspension with acetic acid by mixing about 70% of the molar equivalent of calcium carbonate, taken as free calcium carbonate in the limestone, with the full complement of acetic acid and then adding to this mixture about 30% of the molar equivalent of the calcined limestone base (both calcium and magnesium bases) to produce a calcium magnesium acetate salt solution having a calcium-to-magnesium mole ratio much greater than one, removing substantially all insolubles from said salt solution, calcining said separated insolubles and reacting said calcined insolubles with acetic acid to produce a calcium magnesium acetate solution having a calcium-to-magnesium mole ratio substantially equal to one.

A further process limitation involves initially stockpiling the raw material limestone into two stockpiles, one having a magnesium content greater than a predetermined amount and the other having a magnesium content less than said predetermined amount. The first stockpile is then used as the initial 70 mol% base reactant with acetic acid while the second stockpile is calcined and added to the reaction mixture as 30 mol% base reactant to complete the acetic acid-calcium magnesium carbonate, acid-base reaction.

A still further process variable involves removal of substantially all undissociated acetic acid from the final product. This can be accomplished for example through appropriate adjustment of the final liquor pH to a value between 7 and 8.

BRIEF DESCRIPTION OF THE DRAWING

The FIGURE is a schematic diagram of one specific embodiment of the present invention.

Although specific forms of the invention have been selected for illustration in the drawings, and although specific terms will be used in this specification in describing the features illustrated therein, these are not intended to define or to limit the scope of the invention which is defined in the appended claims.

DESCRIPTION OF THE PREFERRED EMBODIMENTS

Although it is entirely possible to manufacture calcium magnesium acetate synthetically using separate sources for the magnesium carbonate and calcium carbonate bases and reacting the separate bases with acetic acid, in commercial practice limestone will be used as the source of both calcium carbonate and magnesium carbonate. In the United States, limestone is predominantly calcite (calcium carbonate) containing minor amounts of dolomite ($CaCO_3 \cdot MgCO_3$). The proportion of dolomite in limestone varies with the source of the limestone and usually ranges from 0 to 20 wt.%. Although there are some known deposits of dolomitic limestone (containing up to 50% magnesium carbonate) they are relatively small in relation to calcite limestone.

According to the processes of the present invention, limestone containing both calcite and dolomite is reacted with acetic acid using excess acetic acid in relation to the free calcium carbonate content in the limestone. The calcium carbonate readily reacts with the acetic acid. However, the dolomite ($CaCO_3 \cdot MgCO_3$) is substantially insoluble in acetic acid. Thus, the unreacted dolomite along with any other insolubles are removed, such as by filtering, from the reaction mixture. The remaining clear liquor is further reacted with calcined limestone to produce a neutral or nearly neutral calcium magnesium acetate solution. Thus, the reaction proceeds in two steps: the first step being reaction of the limestone with acetic acid followed by reaction with the calcined limestone (lime) in order to complete the reaction between calcium and magnesium carbonate and acetic acid.

In a simple acid-base reaction between acetic acid and either calcium or magnesium carbonate, one of the following two reactions takes place:

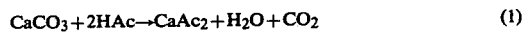

$$CaCO_3 + 2HAc \rightarrow CaAc_2 + H_2O + CO_2 \quad (1)$$

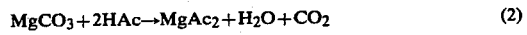

$$MgCO_3 + 2HAc \rightarrow MgAc_2 + H_2O + CO_2 \quad (2)$$

In both of the above two reactions, two moles of acetic acid react with one mole of carbonate. Thus, if one mole of either magnesium or calcium carbonate (in the form of an aqueous solution) comprises the base reactant, two moles of acetic acid reactant are required to completely react with the base.

I have discovered that it is highly advantageous to utilize about 70 mol% of the base carbonate as a calcium and magnesium carbonate mixture having a high magnesium-to-calcium mole ratio and the remaining 30 mol% of the base as a calcium and magnesium carbonate mixture having a low magnesium-to-calcium mole ratio. This can be accomplished by initially stockpiling limestone into two categories, one having a relatively high magnesium content and the other having a relatively low magnesium content. The high magnesium content limestone is reacted with acetic acid in the first step of the reaction while the low magnesium content limestone is calcined and used to "finish off" the reaction to form the first product solution.

The high magnesium and low magnesium content limestone stockpiles are formed by selecting a predetermined magnesium content in the available ores. For example, limestone containing more than 5 wt.% magnesium oxide would be placed in the high magnesium limestone stockpile while limestone containing less than 5 wt.% magnesium oxide would be placed in the low magnesium stockpile. Of course, other predetermined values may be utilized depending on the magnesium content range in the available ores.

Referring to FIG. 1, raw limestone ore is initially separated into two stockpiles, one having a relatively high magnesium content and the other having a relatively low magnesium content. The high magnesium content ore is slurried with water and is added to a reaction vessel and comprises 70 mol% of the base reactant. To this slurry is added acetic acid, preferably in a slight molar excess of three to five percent. After reaction between the high magnesium limestone slurry and the acetic acid, the unreacted dolomite insolubles are removed from the slurry. The clear liquid remaining is then further reacted with a low magnesium content, calcined limestone (lime) which comprises 30 mol% of the base reactant. The product from this first reaction is a calcium magnesium acetate product having a calcium-to-magnesium mole ratio much greater than one.

Any acetic acid remaining in the insolubles removed from the first reaction solution should be recovered by washing. This is essential to conserve this valuable raw material.

The washed unreacted dolomite is then calcined and slurried and further reacted with acetic acid in a second reaction vessel. The product from the second reaction vessel is a calcium magnesium acetate salt solution having a calcium-to-magnesium mole ratio substantially equal to one. The salt solution is also preferably adjusted to a pH of between 7 and 8 in order to minimize the concentration of undissociated acetic acid therein.

Both calcium magnesium acetate salt solutions are then fed to a conventional flaking apparatus to convert them into solid flakes for applications such as road deicing.

Although this invention has been described in connection with specific forms thereof, and with respect to specific steps of the methods herein involved, it will be appreciated that a wide variety of equivalents may be substituted for those specific elements shown and described herein, that certain features may be used independently of other features, and that certain parts and method steps may be reversed, all without departing from the spirit and scope of this invention as described in the appended claims.

I claim:

1. In a process of making different grades of calcium magnesium acetate, having substantially uniform but different calcium-to-magnesium mole ratios, from limestone having varying proportions of calcium carbonate and magnesium carbonate, the steps comprising:
    a. finely dividing limestone containing calcium carbonate and magnesium carbonate;
    b. mixing said finely divided limestone with water to form an aqueous suspension of calcium carbonate and magnesium carbonate;
    c. calcining some finely divided limestone;
    d. reacting an effective amount of said aqueous suspension not above about 70% of the molar equivalent of base with acetic acid and an effective amount of the calcined limestone not below about 30% of the molar equivalent of base to produce a calcium magnesium acetate salt solution having a calcium-to-magnesium mole ratio much greater than one;
    e. separating from said solution substantially all insolubles containing calcium carbonate and magnesium carbonate;
    f. calcining said separated insolubles;
    g. mixing said calcined insolubles with water to form an aqueous lime suspension; and
    h. reacting said lime suspension with acetic acid to produce a calcium magnesium acetate salt solution having a calcium-to-magnesium mole ratio substantially equal to one.

2. The process as defined in claim 1, wherein said finely divided limestone (a) contains magnesium oxide in an amount greater than a predetermined amount and said limestone (b) contains magnesium oxide in an amount less than said predetermined amount.

3. The process as defined in claim 1, wherein said insolubles are removed by filtration of said calcium magnesium acetate solution (d).

4. The process as defined in claim 1, wherein substantially all undissociated acetic acid is washed from said separated insolubles.

5. The process as defined in claim 2, wherein said predetermined amount comprises about 5 wt.%.

6. The process as defined in claim 1, wherein said calcium magnesium acetate salt solution has a pH value in the range from about 7 to about 8.

* * * * *